US00PP36585P3

(12) United States Plant Patent
Volz et al.

(10) Patent No.: US PP36,585 P3
(45) Date of Patent: Apr. 8, 2025

(54) APPLE TREE NAMED 'HOT141A1'

(50) Latin Name: *Malus domestica*
Varietal Denomination: HOT141A1

(71) Applicants: The New Zealand Institute for Plant and Food Research Limited, Auckland (NZ); Institut De Recerca I Tecnologia Agroalimentaries (IRTA), Barcelona (ES); FruitFutur A.I.E, Lledia (ES)

(72) Inventors: Richard Volz, Havelock North (NZ); Lidia Lozano, Lleida (ES)

(73) Assignees: The New Zealand Institute for Plant and Food Research Limited, Auckland (NZ); Institut De Recerca I Tecnologia Agroalimentaries (IRTA), Barcelona (ES); FruitFutur A.I.E., Lleida (ES)

( * ) Notice: Subject to any disclaimer, the term of this patent is extended or adjusted under 35 U.S.C. 154(b) by 0 days.

(21) Appl. No.: 18/831,022

(22) Filed: May 1, 2024

(65) Prior Publication Data

US 2024/0373769 P1 Nov. 7, 2024

Related U.S. Application Data

(60) Provisional application No. 63/464,043, filed on May 4, 2023.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

PUBLICATIONS

U.S. Appl. No. 18/831,023, filed May 1, 2024.
U.S. Appl. No. 18/831,021, filed May 1, 2024.

*Primary Examiner* — Susan McCormick Ewoldt
(74) *Attorney, Agent, or Firm* — LEYDIG, VOIT & MAYER, LTD.

(57) ABSTRACT

A new and distinct apple variety is described. The variety results from crossing the apple varieties 'Cripps Pink' (U.S. Plant Pat. No. 7,880) and 'Scilate' (U.S. Plant Pat. No. 20,477) in Havelock North, New Zealand. The fruit of the apple tree of this new variety have an attractive appearance characterized by its dark red color and it notable for its long storage life. This new variety has been named 'HOT141A1'.

3 Drawing Sheets

Genus and species plant named: *Malus domestica.*
Variety denomination: 'HOT141A1'.

BACKGROUND OF THE INVENTION

The new plant variety described herein resulted from a selection from a population of seedlings derived from the controlled crossing of the apple varieties 'Cripps Pink' (U.S. Plant Pat. No. 7,880) (seed parent) and 'Scilate' (U.S. Plant Pat. No. 20,477) (pollen parent). The planned cross was made in 2005 on trees located in Havelock North, Hawke's Bay, New Zealand and the seed transported and sown in plots in Gimenells near Lleida, Catalonia, Spain. 'HOT141A1' was selected in 2010 as a single plant from among a population of seedlings and was selected for its attractive appearance, good flavor, texture and storage. It was asexually propagated first in Lleida, Spain by budding onto M9 rootstock (unpatented). The variety has since been observed over three asexually propagated generations and found to remain true to type.

SUMMARY OF THE INVENTION

'HOT141A1' is characterized by its attractive fruit with firm texture and high balanced flavor, harvesting in late October in Spain. Under growing conditions in Spain 'HOT141A1' is distinguished from other apple varieties due to the following unique characteristics: Compared to 'Cripps Pink', 'HOT141A1' has an earlier harvest season and a higher proportion of overcolour.

Under the growing conditions in Spain the new variety was able to be distinguished from its parents 'Cripps Pink' and 'Scilate', by the following characteristics:

The harvest season of 'HOT141A1' is approximately 2 weeks earlier than that of 'Cripps Pink'.

'HOT141A1' has a fruit skin overcolour pattern of a solid flush with weakly defined stripes; compared to 'Cripps Pink' which has a solid flush overcolour pattern. 70% of the skin surface of HOT141A1 is covered by red overcolour, compared to 'Cripps Pink' which has 50-60% pink overcolour.

Asexual reproduction of this new variety by budding and grafting shows that the aforementioned characteristics are true to form and are established and transmitted through succeeding propagation. This is true of buds grafted onto M9 rootstocks.

BRIEF DESCRIPTION OF PHOTOGRAPHS

The accompanying photographs show typical specimens of the tree, foliage and fruit of the new variety as depicted in colours as nearly true as is reasonably possible to make the same in a colour illustration of this character.

DETAILED DESCRIPTION

Figure 1:
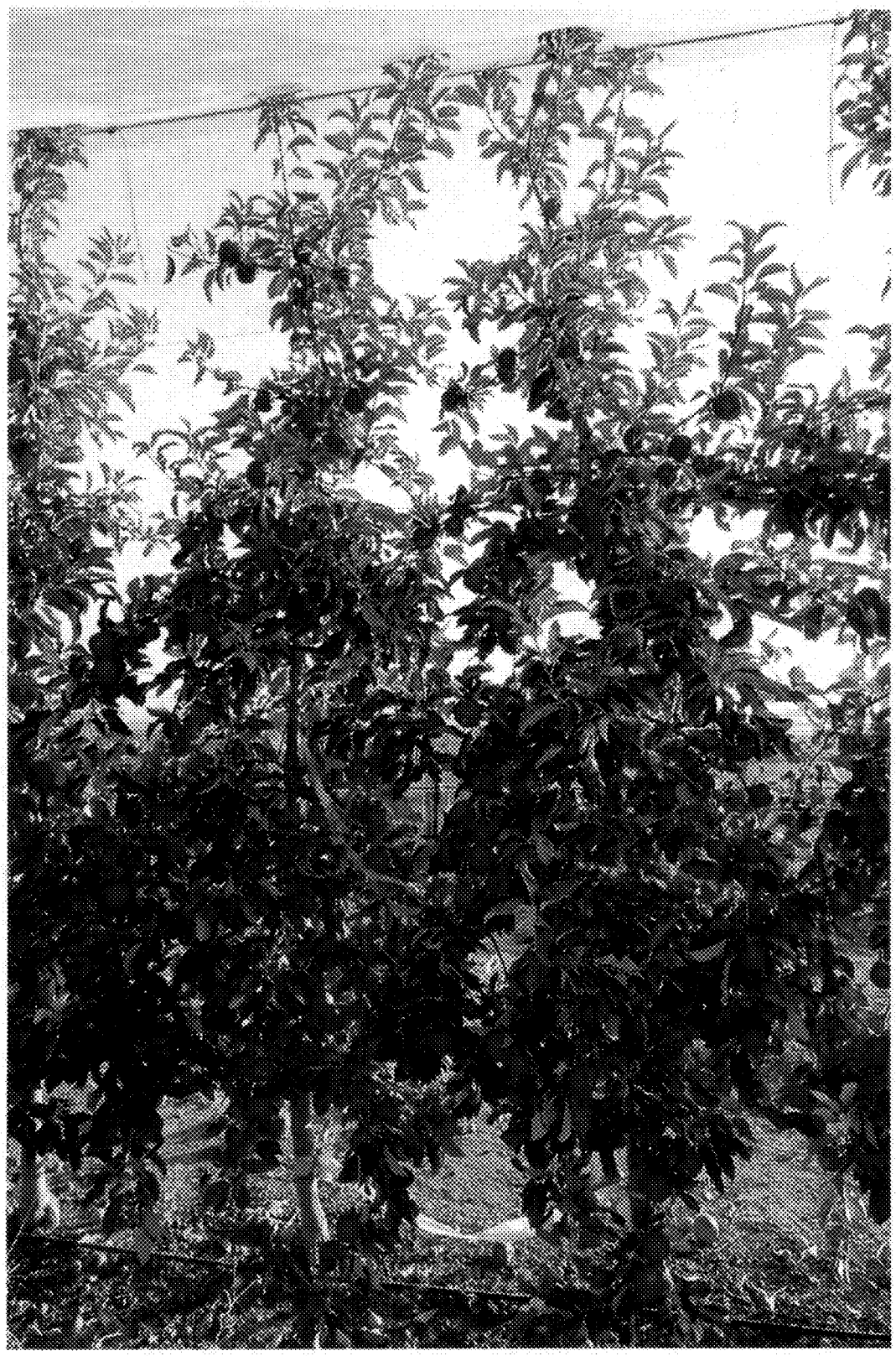
FIG. 1 shows a 3-year-old tree of 'HOT141A1' scion on M9 rootstock in the field.
Figure 2:
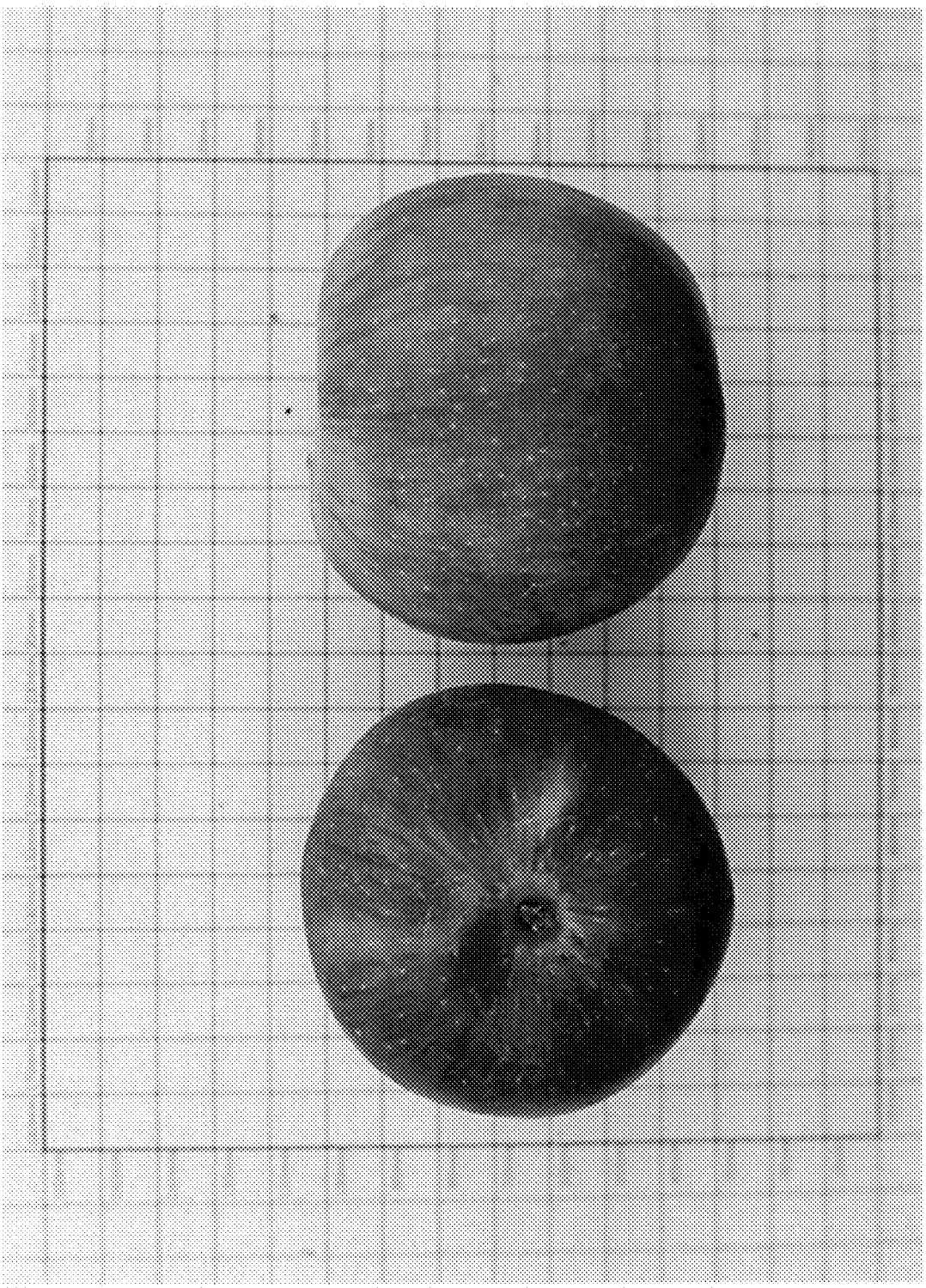
FIG. 2 shows whole 'HOT141A1' fruit.
Figure 3:
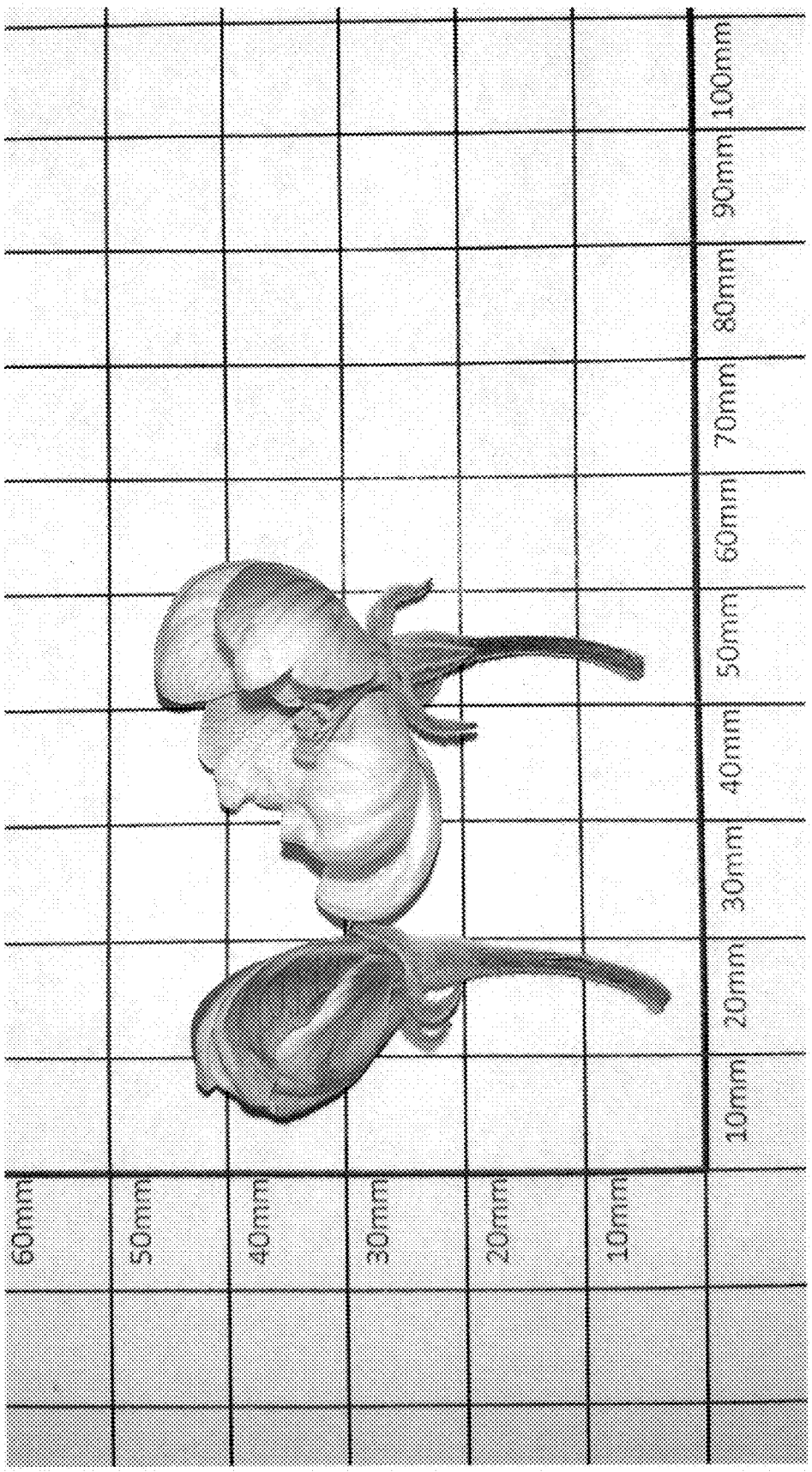
FIG. 3 shows 'HOT141A1' flower.

The following is a description of the new variety with colour terminology in accordance with The Royal Horticultural Society Colour Charts (R.H.S.C.C.) sixth edition (2015).

The specimens described were grown at Lleida, Catalonia, Spain. The observations were made over several seasons from 2018-2020 season on 5-9 year old trees.

Tree: Ramified growth habit, approximately 3.25 m tall and 1.35 m wide; spreading habit; bearing on spurs and long shoots; medium vigor on M9 rootstock (unpatented), managed under standard orchard practice.

Trunk: Measurements were taken 20 cm from the graft union. Trunk circumference approximately 18.4 cm; color dark grayish yellow 199D; bark texture fine granulated.

One year old shoot: Approximately 38.36 cm long, thin with straight growth; colour on the sunny side brownish orange 166C; average internode length 3.05 mm; number of lenticels were sparse, round in shape and yellowish white 155B and approximately 0.814 mm in diameter.

Leaves: Average length 110.894 mm; average width 63 mm at the widest point; upper side of the blade moderate olive green N147A; underside moderate yellow green 147B with medium pubescence; basal shape right angled; apex shape right acute; margin of the leaves biserrate; the attitude in relation to the shoot upwards. Vegetative bud burst early March.

Petiole: Average length 29.712 mm; average width 2.39 mm. Upper side colour moderate yellow green 146D; under side colour moderate yellow green 146D.

Stipule: Average length 14.236 mm; average width 2.21 mm; shape banana; colour moderate olive green 147A on the upper side; under side colour of the stipules moderate yellow green 147B.

Flowers: Diameter of the open flower approximately 28.9 mm; petals were not touching, and there were five flowers per cluster; time of beginning of flowering late March, followed by full bloom on the approximately 1st April.

Petals: Five petals per flower with a broad ovate shape; average length 12.7 mm; average width 8.9 mm; with a cuneate base; colouration strong reddish purple 70B with strong purplish red veins 63B.

Stamen: Average of 20 per flower. Filaments greenish white 155C and average length 6.17 mm. Anthers average length of 2.27 mm; average width 1.2 mm; colour light yellow 11B. Pollen colour brilliant greenish yellow 3A. Anther position below stigma.

Pedicel: Average length 17.69 mm; average diameter 1.43 mm; colour moderate yellow green 146C.

Sepals: Five sepals per flower; overall shape of an acute and curved triangle; smooth margin; average length 6.13 mm; average width 3.38 mm; colour strong yellow green 144A.

Fruit size: Large to very large; average width 90 mm; average height 87.168 mm; average weight 299 g.

Shape: Conic; position of maximum diameter slightly towards stalk; crowning at calyx end moderate. Eye basin average depth 12.208 mm; average width 32.376 mm.

Skin: Soft texture; ribbing absent or weak; bloom of skin absent or weak; greasiness of skin absent or weak; background colour light greenish yellow 1C; number of lenticels medium; size of lenticels medium.

Overcolour: Approximately 70% of skin surface; dark red 183A; pattern of overcolour flushed striped mottled; width of stripes medium; large amount of russet around stalk cavity; amount of russet on cheeks absent or small; area of russet around eye basin absent or small.

Stalk: Average length 16.535 mm; average width 2.9 mm; curvature medium. Average depth of stalk cavity 22.818 mm; average width 38.018 mm.

Flesh: Firm, average fruit firmness 7.8 kgf; very juicy; colour pale yellow 11D.

Flavor: Balanced and fennel hint; aroma fennel; soluble solids 14.5%.

Seeds: Five locules; medium seed size; average length 10 mm; average width 5.206 mm; colour greyish reddish brown 200B.

Harvest: Late October.

Use: Dessert. Adapted to hot climate growing conditions. Less sensitive to sunburn than 'Cripps Pink' and 'Scilate'.

Keeping quality: Excellent, up to 8 months at 0.5° C.+1 week shelf life.

The invention claimed is:

1. A new and distinct variety of apple tree named 'HOT141A1' substantially as illustrated and described herein.

* * * * *